United States Patent
Shimuta

(10) Patent No.: US 10,884,160 B2
(45) Date of Patent: Jan. 5, 2021

(54) STICK-ON SENSOR DEVICE FOR DETERMINING LIVING BODY ABNORMALITY

(71) Applicant: Murata Manufacturing Co., Ltd., Kyoto (JP)

(72) Inventor: Toru Shimuta, Kyoto (JP)

(73) Assignee: MURATA MANUFACTURING CO., LTD., Kyoto (JP)

(*) Notice: Subject to any disclaimer, the term of this patent is extended or adjusted under 35 U.S.C. 154(b) by 0 days.

(21) Appl. No.: 16/795,672

(22) Filed: Feb. 20, 2020

(65) Prior Publication Data
US 2020/0271824 A1    Aug. 27, 2020

(30) Foreign Application Priority Data
Feb. 26, 2019   (JP) .................. 2019-032356

(51) Int. Cl.
| | |
|---|---|
| *G01V 8/20* | (2006.01) |
| *G01K 13/00* | (2006.01) |
| *A61B 5/00* | (2006.01) |
| *A61B 5/01* | (2006.01) |

(52) U.S. Cl.
CPC .................. *G01V 8/20* (2013.01); *A61B 5/01* (2013.01); *A61B 5/6833* (2013.01); *A61B 5/6844* (2013.01); *G01K 13/002* (2013.01)

(58) Field of Classification Search
CPC .......... G01V 8/20; A61B 5/01; A61B 5/6833; A61B 5/6844; G01K 13/002

USPC ........................................................ 356/432
See application file for complete search history.

(56) References Cited

U.S. PATENT DOCUMENTS

2017/0052127 A1* 2/2017 Kobayashi ........ H01L 27/14625

FOREIGN PATENT DOCUMENTS

| JP | 2009-229117 A | 10/2009 |
|---|---|---|
| JP | 2012-154859 A | 8/2012 |

* cited by examiner

*Primary Examiner* — Roy M Punnoose
(74) *Attorney, Agent, or Firm* — Pearne & Gordon LLP

(57) ABSTRACT

A stick-on deep body thermometer includes a light emitting unit emitting detection light, a first scattering portion scattering the detection light passing a light-transmissive lower exterior body, a first adhesive layer that is adhesive, light-transmissive, and stuck on the lower exterior body, where the detection light scattered by the first scattering portion enters, a second scattering portion scattering detection light propagating in the first adhesive layer, a light receiving unit receiving detection light scattered by the second scattering portion, passing the lower exterior body, and incident thereon, and a contact state determination unit determining the stick-on deep body thermometer and a living body surface are in contact when a light receiving amount of the detection light is under a predetermined value, and determining they are not in contact when the light receiving amount of the detection light is not under the predetermined value.

20 Claims, 9 Drawing Sheets

STICK-ON SENSOR DEVICE FOR DETERMINING LIVING BODY ABNORMALITY

This application claims priority from Japanese Patent Application No. 2019-032356 filed on Feb. 26, 2019. The content of this application is incorporated herein by reference in its entirety.

BACKGROUND

The present disclosure relates to a stick-on device used while being stuck on a living body. In the past, there have been proposed various types of stick-on devices used while being stuck on a living body. For example, Japanese Unexamined Patent Application Publication No. 2012-154859 discloses a stick-on body thermometer for measuring a deep body temperature of a subject while being stuck on a body surface of the subject.

More specifically, the body thermometer includes first and second thermal resistors each provided with a first temperature sensor disposed on one side surface in contact with the body surface and a second temperature sensor disposed on another side surface facing the one side surface, a homogenizing member configured to cover only the other side surfaces of the respective first and second thermal resistors, a heat insulating member disposed so as to surround side surfaces of the respective first and second thermal resistors, and a protective member provided such that a circumference portion is fixed on another side surface of the heat insulating member, and a central portion is disposed sandwiching a predetermined space with the homogenizing member. Further, an entire body surface side of the body thermometer is covered with a sticking tape.

According to the body thermometer described in Japanese Unexamined Patent Application Publication No. 2012-154859, since the entire body surface side of the body thermometer is covered with the sticking tape, it is possible to easily attach the body thermometer on the body surface of the subject. However, since the body thermometer is stuck on the body surface with the sticking tape, the body thermometer may come off from the body surface during measurement. Thus, there has been a demand to detect a contact state (attachment/detachment) of the body thermometer.

On the other hand, various contact detection methods have been proposed in the past. For example, Japanese Unexamined Patent Application Publication No. 2009-229117 discloses a contact detection method such as an optical method, an electrostatic capacity method or the like. More specifically, Japanese Unexamined Patent Application Publication No. 2009-229117 discloses a contact detection method that includes, for example, a plurality of light sources disposed in a hollow interior of a probe, and a plurality of light receiving units disposed in the hollow interior of the probe, the probe includes a window portion through which light emitted by the light source can be transmitted outward the probe, and a determination unit determines whether a contact state between a temperature measuring unit and a portion of a user to be measured is good or bad, based on a change in an amount of light received by the plurality of light receiving units.

According to the contact detection method described in Japanese Unexamined Patent Application Publication No. 2009-229117, when the probe is held under the armpit or the like of the user, light passing through the window portion is reflected by part of a body of the user covering an outside of the window portion and returns to the hollow interior of the probe, so that the amount of light received by the light receiving unit arranged in the hollow interior of the prove increases. On the other hand, when the probe is not held under the armpit or the like of the user, or when the holding is insufficient, light emitted by a light emitting unit is transmitted through the window portion to leak out to the outside of the probe, so that the amount of light received by the light receiving unit disposed in the hollow interior of the probe decreases. Thus, a contact state between the probe and a human body can be evaluated, based on a change in the amount of light received by the light receiving unit.

However, in the contact detection method described above, when the stick-on device is slightly separated from a living body surface, reflected light may return, and thus, there is a possibility that it is impossible to correctly detect the contact state, that is, whether they are in contact with each other or not.

BRIEF SUMMARY

The present disclosure provides a stick-on device used while being stuck on a living body, that can reliably determine whether the stick-on device is in contact with the living body or not, in particular, even in a state of being slightly separated from the living body surface.

A stick-on device according to embodiments of the present disclosure is a stick-on device used while being stuck on a living body that includes, a light emitting unit, disposed inside the stick-on device, for emitting detection light, a first scattering portion for scattering the detection light emitted from the light emitting unit and transmitted through a lower exterior body that is light-transmissive of the stick-on device, an adhesive member that has adhesiveness and is light transmissive, is stuck on the lower exterior body, and on which the detection light scattered by the first scattering portion is incident, a second scattering portion for scattering the detection light propagated in the adhesive member, a light receiving unit, disposed inside the stick-on device, for receiving the detection light scattered by the second scattering portion, transmitted through the lower exterior body, and incident on the light receiving unit, and a determination unit for, when a light receiving amount of the detection light received by the light receiving unit is less than a predetermined value, determining that the stick-on device and the living body surface are normally in contact with each other, and when the light receiving amount of the detection light received by the light receiving unit is equal to or larger than the predetermined value, determining that a contact state between the stick-on device and the living body surface is abnormal.

According to the stick-on device according to embodiments of the present disclosure, the detection light emitted from the light emitting unit is scattered by the first scattering portion, and is incident on the adhesive member. Then, after propagating in the adhesive member, the detection light is scattered by the second scattering portion, is transmitted through the lower exterior body, reaches the light receiving unit, and is received by the light receiving unit. Incidentally, since a refractive index of a skin is closer to a refractive index of the adhesive member compared to air, when the body surface comes in contact with the adhesive member, leakage of the detection light to the body surface increases, and the amount of light received by the light receiving unit decreases. Thus, when the light receiving amount of the received detection light is less than the predetermined value, it is possible to determine that the adhesive member, that is, the stick-on device, and the living body surface are normally in contact with each other, and when the light receiving amount of the received detection light is equal to or more than the predetermined value, it is possible to determine that the contact state between the stick-on device and the living body surface is abnormal.

Other features, elements, characteristics and advantages of the present disclosure will become more apparent from the following detailed description of embodiments of the present disclosure with reference to the attached drawings.

DETAILED DESCRIPTION

Figure 1:
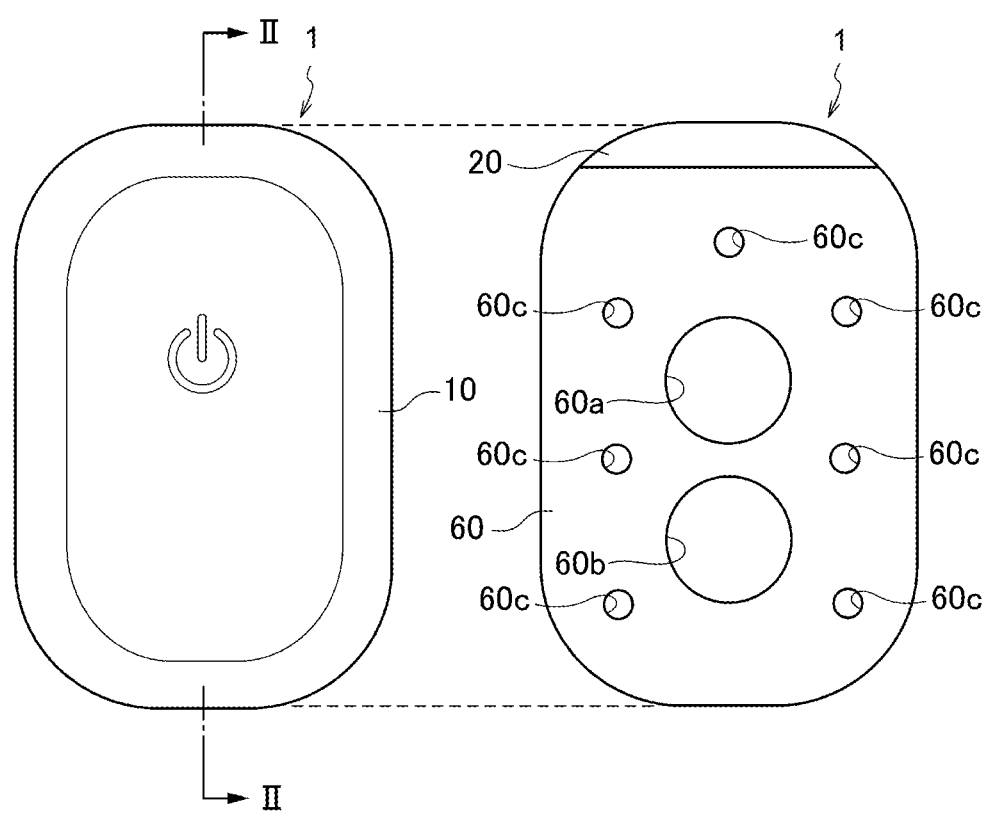
FIG. 1 includes a plan view and a bottom view illustrating an appearance of a stick-on deep body thermometer according to a first embodiment.

Hereinafter, embodiments of the present disclosure will be described in detail with reference to the accompanying drawings. In the drawings, the same reference numerals are used to designate the same or corresponding parts. In each drawing, the same elements are denoted by the same reference numerals, and the description thereof will not be repeated. Here, a stick-on non-heating type deep body thermometer will be described as an example of a stick-on device according to the embodiments of the present disclosure.

First Embodiment

Figure 2:
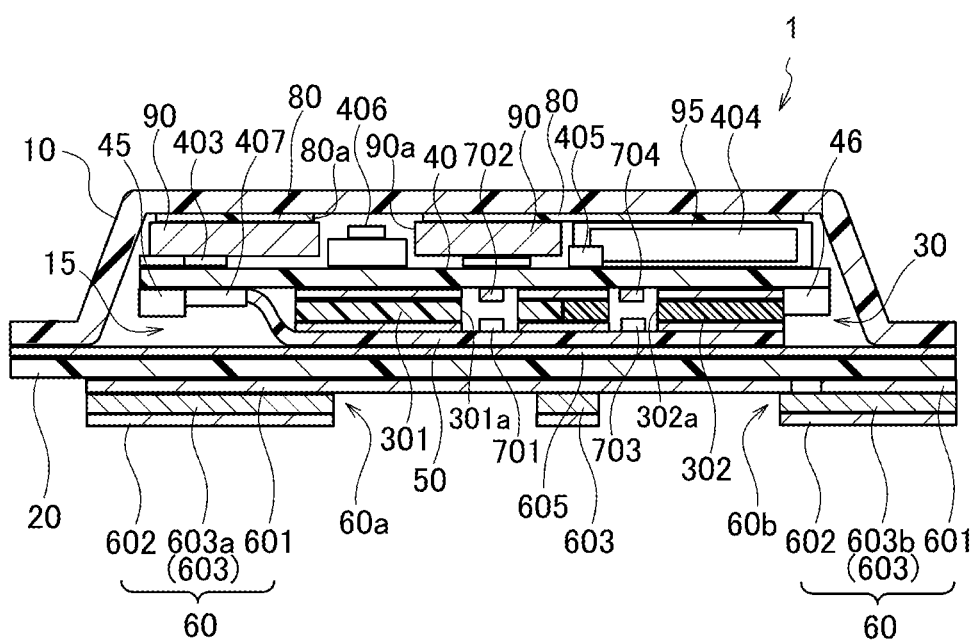
FIG. 2 is a sectional view illustrating a configuration of the stick-on deep body thermometer according to the first embodiment.
Figure 3:
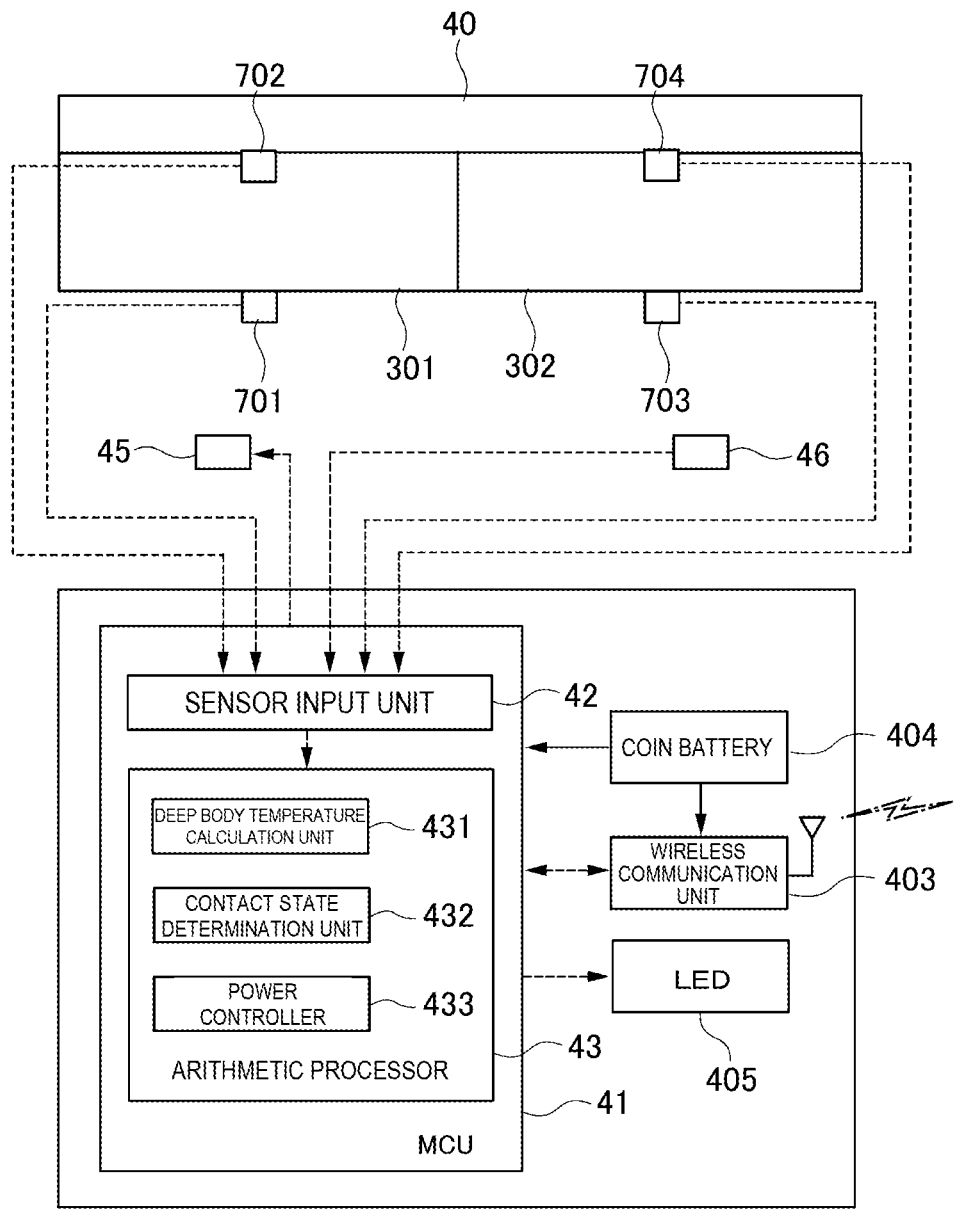
FIG. 3 is a block diagram illustrating a functional configuration of a processor constituting the stick-on deep body thermometer according to the first embodiment.
Figure 4:
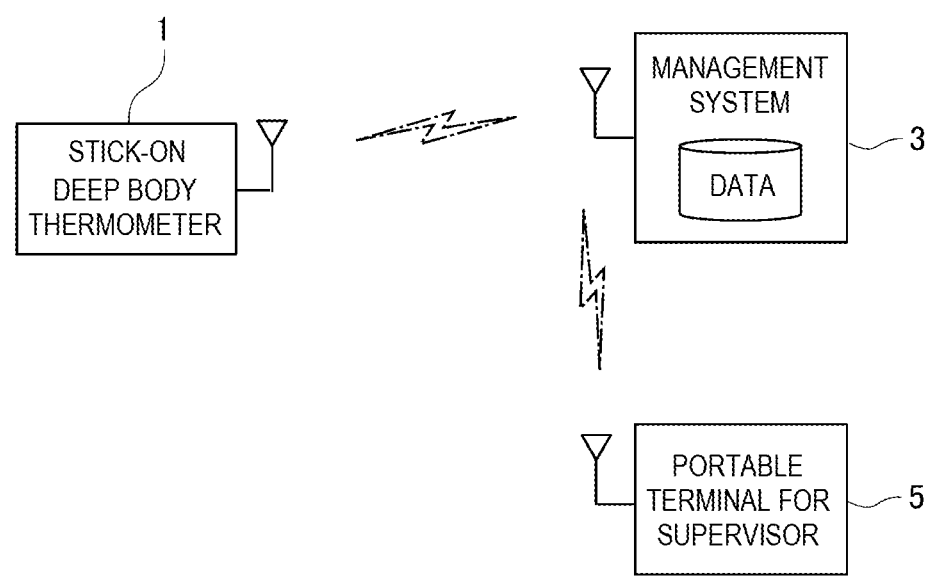
FIG. 4 is a block diagram illustrating an overall configuration of a deep body temperature measurement system to which the stick-on deep body thermometer according to the first embodiment is applied.

First, FIG. 1 to FIG. 4 are used together to describe a configuration of a stick-on deep body thermometer (hereinafter simply referred to as a "deep body thermometer" or a "body thermometer" in some cases) 1 according to a first embodiment. FIG. 1 includes a plan view and a bottom view illustrating an appearance of the stick-on deep body thermometer 1. FIG. 2 is a sectional view (sectional view taken along a line II-II in FIG. 1) illustrating the configuration of the stick-on deep body thermometer 1. FIG. 3 is a block diagram illustrating a functional configuration of a processor 41 constituting the stick-on deep body thermometer 1. FIG. 4 is a block diagram illustrating an overall configuration of a deep body temperature measurement system to which the stick-on deep body thermometer 1 is applied.

The deep body thermometer 1 is a non-heating type deep body thermometer for obtaining a heat flow from a deep portion of a user (subject) based on a difference between respective temperatures detected by a first temperature sensor 701 and a second temperature sensor 702, and a difference between respective temperatures detected by a third temperature sensor 703 and a fourth temperature sensor 704, and acquiring a deep body temperature. Further, the deep body thermometer 1 is a stick-on deep body thermometer that is stuck on a body surface of the user, and continuously measures a body temperature to acquire body temperature data.

The deep body thermometer 1 is configured to mainly include an upper exterior body 10, a lower exterior body 20, a body temperature measuring unit 15, a lining member 80, a buffer member 90, and a sticking member 60. In addition, the body temperature measuring unit 15 is configured to mainly include a thermal resistor layer 30, a wiring substrate 40 in or on which the second temperature sensor 702 and the fourth temperature sensor 704 are mounted, and a flexible substrate 50 in or on which the first temperature sensor 701 and the third temperature sensor 703 are mounted.

The upper exterior body 10 is formed of, for example, a closed cell or semi-closed cell foam material having a waterproof property and a heat retaining property. In order to prevent a temperature of the body temperature measuring unit 15 from locally changing due to a sudden change in an outside-air temperature, a foam material having low thermal conductivity can be used for the upper exterior body 10. Note that, as the material, for example, polyurethane, polystyrene, polyolefin or the like is suitably used. Further, as a method for processing the upper exterior body 10, for example, vacuum molding is suitably used. The upper exterior body 10 is formed in a substantially hat shape in a cross section so that the body temperature measuring unit 15 (the thermal resistor layer 30, the wiring substrate 40, the flexible substrate 50, and the like) can be accommodated therein. Thus, a side surface of the thermal resistor layer 30 is covered with the foam material, and the side surface of the thermal resistor layer 30 is prevented from being exposed to the outside air.

The lower exterior body 20 is formed of, for example, a non-foaming resin film having the waterproof property, and higher thermal conductivity than that of the upper exterior body 10. Further, the lower exterior body 20 is formed of a transparent or translucent material so as to be light-transmissive. Note that, from a viewpoint of suppressing propagation of detection light in the lower exterior body 20 and improving detection sensitivity for contact with a living body, the lower exterior body 20 can be translucent. Examples of the material for the lower exterior body 20 include, for example, polypropylene, polyethylene, polyester, polyimide and the like, and polyethylene terephthalate (PET) is particularly suitably used.

The lower exterior body 20 is formed in a planar shape so that the flexible substrate 50 (body temperature measuring unit 15) in or on which the first temperature sensor 701 and the third temperature sensor 703 are mounted can be fixed in close contact. Note that, since thermal resistance is changed when a gap is generated between the body temperature measuring unit 15 and the lower exterior body 20 to affect a heat flux, the body temperature measuring unit 15 and the lower exterior body 20 are stuck to each other by a double-sided tape 605, and are fixed in close contact. Note that, instead of the method of sticking with the double-sided tape 605, for example, a method of fixing by an adhesive or the like may be used to fix in close contact. Respective sizes (outer dimensions) of the upper exterior body 10 and the lower exterior body 20 are formed to be the same or substantially the same, and are formed to have a size of, for example, about 40 to 100 mm in length, and about 20 to 60 mm in width.

Then, a peripheral edge portion of the upper exterior body 10 formed in the substantially hat shape in a cross section, and a peripheral edge portion of the lower exterior body 20 formed in the planar shape are fixed in close contact with each other by, for example, sticking with a double-sided tape, fixing with an adhesive, heat sealing, or the like. Note that, in the present embodiment, the double-sided tape 605 is used for sticking. Here, in order to realize waterproof performance, a portion where the upper exterior body 10 and the lower exterior body 20 are fixed in close contact with each other is desirably flat and has structure in which wrinkles are less likely to be formed. That is, an outer edge portion of the lower exterior body 20 can be flat and an outer edge portion of the opposed upper exterior body 10 be also flat, and that the outer edge portions be stuck and fixed in close contact with each other. In this way, since force is uniformly applied to the portion of close contact fixing, a problem, such as formation of wrinkles, is unlikely to occur that adversely affects the waterproof performance.

As illustrated in FIG. 2, the body temperature measuring unit 15 is configured by laminating the flexible substrate 50, the thermal resistor layer 30, and the wiring substrate 40 in this order from a side of the lower exterior body 20.

The thermal resistor layer 30 has, in order to form two heat fluxes, two thermal resistors that have thermal resistance values different from each other, that is, a first thermal resistor 301 and a second thermal resistor 302. For the first thermal resistor 301, a material having thermal conductivity higher than that of the second thermal resistor 302, that is, a material having a low thermal resistance value, for example, plastics such as a polypropylene resin, a polyethylene resin, an acrylic resin, a polycarbonate resin, an epoxy resin or the like, are suitably used. For the second thermal resistor 302, a material having thermal conductivity lower than that of the first thermal resistor 301, that is, a material having a high thermal resistance value, for example, foamed plastics such as polyurethane, polystyrene, polyolefin, or the like, are suitably used. However, plastic or rubber which is not foamed may also be used. Note that, here, thermal conductivity of metal such as copper, aluminum or the like is about 100 [W/m/K] or more, whereas thermal conductivity of plastics such as a polypropylene resin, a polyethylene resin, an acrylic resin, a polycarbonate resin, an epoxy resin or the like is about 0.1 to 0.5 [W/m/K], and is about 1000 times smaller. Thermal conductivity of foamed plastic is about 10 times further smaller. Thermal conductivity of air is further smaller and is about 0.024 [W/m/K]. The first thermal resistor 301 and the second thermal resistor 302 are formed to have substantially the same thickness, in order to reduce cost by enabling the wiring substrate 40 and the flexible substrate 50 to be laminated on each other.

The first thermal resistor 301 constituting the thermal resistor layer 30 is formed with a through-hole 301a penetrating in a thickness direction. Similarly, the second thermal resistor 302 constituting the thermal resistor layer 30 is formed with a through-hole 302a penetrating in a thickness direction. The through-hole 301a is formed so that, in a plan view, the first temperature sensor 701 and the second temperature sensor 702 are housed inside thereof. That is, a pair of the first temperature sensors 701 and the second temperature sensor 702 is disposed inside the through-hole 301a along a thickness direction of the first thermal resistor 301. Similarly, the through-hole 302a is formed so that, in a plan view, the third temperature sensor 703 and the fourth temperature sensor 704 are housed inside thereof. That is, a pair of the third temperature sensors 703 and the fourth temperature sensor 704 is disposed inside the through-hole 302a along a thickness direction of the second thermal resistor 302.

Here, as the first temperature sensor 701 to the fourth temperature sensor 704 (hereinafter, sometimes collectively referred to as a "temperature sensor 70"), for example, a thermistor, a temperature measuring resistor, or the like, whose resistance value varies depending on temperature, is suitably used. Note that, the temperature sensor 70, from a viewpoint of enhancing responsiveness, can have as small heat capacity as possible. Thus, a chip thermistor is suitably used as the temperature sensor 70, for example. Each of the first temperature sensor 701 to the fourth temperature sensor 704 is electrically connected to the processor 41 (processing circuit), which will be described later, with a printed wiring interposed therebetween, and an electric signal (for example, a voltage value) corresponding to temperature is read by the processor 41.

Incidentally, in order to reduce a size of the deep body thermometer 1 of a thermal flow type, it becomes important to make the thermal resistor layer 30 (first thermal resistor 301 and second thermal resistor 302) smaller. When the thermal resistor layer 30 is made to be smaller, however, a difference in respective output values of the pair of temperature sensors 70 becomes smaller, so that there is a possibility that a measurement error becomes large. Here, since the temperature sensor 70 (chip thermistor) is a substantially rectangular parallelepiped and has a thickness, the thickness cannot be ignored when the thermal resistor layer 30 is made to be thinner. When the temperature sensor 70 is in contact with a side surface of the thermal resistor layer 30, heat is transmitted from the contact portion, so that there is a possibility that a temperature (detected value) of the temperature sensor 70 may become a temperature different from a surface temperature of the thermal resistor layer 30. Thus, in order to reduce the influence, the through-holes 301a and 302a are formed in the thermal resistor layer 30 around the temperature sensor 70, to obtain structure so that the temperature sensor 70 is not in contact with the side surface of the thermal resistor layer 30.

The wiring substrate 40 is, for example, a rigid substrate such as a glass epoxy substrate. The wiring substrate 40 is mounted with the processor 41 (processing circuit) for processing an output signal from each of the first temperature sensor 701 to the fourth temperature sensor 704 to acquire deep body temperature data, and for processing an output signal of the light receiving unit 46 to determine a contact state with a living body surface. Also, the wiring substrate 40 is mounted with a wireless communication unit 403 for transmitting the acquired deep body temperature data and contact state information indicating the contact state with the living body, and a coin battery 404 for supplying power to the processor 41 and the wireless communication unit 403. The processor 41 mainly includes a sensor input unit 42 (input I/F circuit) and an arithmetic processor 43 (arithmetic processing circuit). The sensor input unit 42, for reading detection signals (for example, an output voltage) of the temperature sensor 70 and the light receiving unit 46, for example, is configured to include an amplifier, an A/D converter, and the like. The sensor input unit 42 amplifies an analog signal outputted from each of the temperature sensors 70 and the light receiving unit 46, converts the amplified analog signal into a digital signal, and outputs the digital signal to the arithmetic processor 43.

The arithmetic processor 43 is constituted by, for example, a micro control unit (MCU), an EEPROM, a RAM, and the like, calculates a deep body temperature from read temperature data, and detects a contact state of the deep body thermometer 1 with the living body. The details will be described later.

In or on a lower surface of the wiring substrate 40, the second temperature sensor 702 for acquiring a temperature of an upper surface (outside air side) of the first thermal resistor 301, and the fourth temperature sensor 704 for detecting a temperature of an upper surface of the second thermal resistor 302 are mounted. More specifically, a pair of thermal homogenizing patterns for homogenizing ambient temperature distribution is formed on the lower surface of the wiring substrate 40, one electrode of the second temperature sensor 702 is connected to one of the thermal homogenizing patterns, and one electrode of the fourth temperature sensor 704 is connected to the other of the thermal homogenizing patterns. The pair of thermal homogenizing patterns is formed, for example, of a material having high thermal conductivity, such as a metal film.

Further, in or on the lower surface of the wiring substrate 40, a light emitting unit 45 including a light emitting element and the light receiving unit 46 including a light receiving element are mounted. Each of the light emitting unit 45 and the light receiving unit 46 is mounted in or on the wiring substrate 40 at a predetermined interval so as to face the lower exterior body 20.

The light emitting unit 45 has the light emitting element, and emits detection light for detecting the contact state with the living body in a direction of the lower exterior body 20. As the light emitting unit 45, for example, an LED, a vertical cavity surface emitting laser (VCSEL), a resonator type LED, or the like can be used. Here, the light emitting unit 45 can emit the detection light that is visible light. In particular, as the detection light, from a viewpoint of improving contact detection performance, blue to yellow green light can be used that is largely absorbed by hemoglobin and is easily absorbed by the living body. That is, light having a wave length of about 500 to 550 nm can be used. In this manner, by using light having a wave length that is largely absorbed by the living body, detection light entering the living body is almost prevented from returning to a first adhesive layer 601, so that leakage of the detection light increases, and the contact detection performance improves. However, when it is not desirable that shining light is visible, light having a wave length invisible to an eye such as near-infrared light may be used.

In addition, the light emitting unit 45 can emit pulsing detection light. Since pulsing light is emitted, power consumption of the light emitting unit 45 can be reduced, and a life of the battery 404 can be extended. For example, when the deep body thermometer 1 is used while being stuck on a skin for a long time, a pulse period (light emission period) from about several tens of seconds to about several minutes is suitable. On the other hand, when a time for sticking on the skin is short (about several minutes), the pulse period of about 1 to 10 seconds is suitable.

The light receiving unit 46 includes the light receiving element, and receives detection light that is scattered by a second scattering portion 603b to be described later, is transmitted through the lower exterior body 20, and is incident thereon. As the light receiving unit 46, for example, a photodiode, a phototransistor, or the like is suitably used. Note that, the light emitting unit 45 and the light receiving unit 46 may be mounted in or on the flexible substrate 50.

Further, in order to prevent only a temperature of part of the wiring substrate 40 from being changed due to influence of an outside-air temperature or the like, a homogenizing member (metal film) having high thermal conductivity for thermally homogenizing influence of temperature distribution of the outside-air temperature can be provided, on a back surface side (outside air side) of a wiring layer in or on which the second temperature sensor 702 and the fourth temperature sensor 704 are mounted. Here, as the homogenizing member, although a metal foil or a metal thin plate may be used, similar to the wiring layer formed in or on the wiring substrate 40, the homogenizing member can be formed as a wiring pattern of an inner layer of the wiring substrate 40 (multilayer rigid substrate). In this case, although the wiring pattern of the inner layer used as the homogenizing member may be a ground pattern, the wiring pattern can be an independent pattern that is not connected to an electric circuit and in which no electric current flows.

The wireless communication unit 403 (corresponding to a transmitting unit described in the claims) transmits the acquired deep body temperature data, and contact state information indicating the contact state of the deep body thermometer 1 with the living body, and the like, to an external management device/management system 3 (corresponding to an external device described in the claims, for example, a server or the like) (refer to FIG. 4). Here, the wireless communication unit 403 transmits, for example, by using Bluetooth (registered trademark) or the like, the deep body temperature data and the contact state information to the external management device/management system 3. When the contact state information is received, the management device/management system 3 can transmit the contact state information to a portable terminal 5 (for example, a smart phone or the like) of an administrator/supervisor (for example, a nurse, a site foreman, or the like). This causes the manager/supervisor to recognize the contact state of the stick-on deep body thermometer 1. Note that, the wireless communication unit 403 may be configured to directly transmit the above contact state information to the portable terminal 5 of the manager/supervisor.

The thin coin battery 404 supplies power to the processor 41, the wireless communication unit 403, and the like, described above. The coin battery 404 is housed in a battery holder 95 mounted in or on the wiring substrate 40. The battery holder 95 is disposed between the wiring substrate 40 and the lining member 80. That is, the battery holder 95 also serves as a spacer member for supporting the lining member 80. Note that, in order to reduce a plane area of the body temperature measuring unit 15 (the deep body thermometer 1), and to suppress influence of heat generated along with a change in the outside-air temperature or operation of the wireless communication unit 403, the wireless communication unit 403 and the coin battery 404 are disposed on an opposite side of the wiring substrate 40 from the temperature sensor 70 (that is, the wireless communication unit 403 and the coin battery 404 are disposed on an upper surface side of the wiring substrate 40).

On an upper surface of the wiring substrate 40, a power switch 406 for accepting a power on/off operation by the user is mounted with the upper exterior body 10 interposed therebetween. The wiring substrate 40 is housed in a sealed space defined by the upper exterior body 10 and the lower exterior body 20 so that the power switch 406 faces a back surface of the upper exterior body 10. As the power switch 406, for example, a push button switch, a rocker switch, or the like is suitably used. Note that, in a case of a push button switch, the push button can perform an alternate operation that holds an on state even when a fingertip is released. Additionally, although the power switch 406 can be a surface mount type, a lead type may also be used.

Here, in order to prevent the power supply switch 406 from being erroneously depressed and power supply from being turned on/off, and in order to prevent the power switch 406 from pushing up the upper exterior body 10, the power switch 406 is disposed so as not to come in contact with the upper exterior body 10. More specifically, an interval between a button upper surface of the power switch 406 and the back surface of the upper exterior body 10 can be, for example, set in a range of about 0 to 4 mm, and can be in a range of about 0.5 to 1.5 mm. Further, a stroke of the power switch 406 can be, for example, set in a range of about 0.1 to 1 mm, and can be set in a range of about 0.1 to 0.3 mm.

Further, in or on the upper surface of the wiring substrate 40, an LED 405 is mounted that is turned on or off in accordance with an operation by the user or a measurement state of a deep body temperature (for example, on/off of the power switch 406, start/end of measurement, the contact state, or the like). Note that, instead of the LED, for example, a VCSEL or the like may be used. Further, an FPC connector 407 for electrically connecting the flexible substrate 50 is attached to a side of the lower surface of the wiring substrate 40.

The flexible substrate (FPC) 50 is formed of, for example, polyimide, polyester (PET), or the like, and has flexibility. The first temperature sensor 701 for acquiring a temperature on a skin side of the first thermal resistor 301, and the third temperature sensor 703 for acquiring a temperature on a skin side of the second thermal resistor 302 are mounted in or on the flexible substrate 50. More specifically, in order to homogenize distribution of ambient temperature, the flexible substrate 50 is formed with a pair of thermal homogenizing patterns, one terminal of the first temperature sensor 701 is connected to one of the thermal homogenizing patterns, and one terminal of the third temperature sensor 703 is connected to the other of the thermal homogenizing patterns. The pair of thermal homogenizing patterns is, for example, formed of a material having high thermal conductivity such as a metal film. Each of the first temperature sensor 701 and the third temperature sensor 703 is connected to the wiring substrate 40 (processor 41) through a wiring pattern and the above FPC connector 407, and an electric signal (voltage value) corresponding to a temperature is read by the processor 41 (sensor input unit 42). Note that, in order to form a heat flux, the lower exterior body 20, the flexible substrate 50, the thermal resistor layer 30, and the wiring substrate 40 are fixed in close contact by, for example, a double-sided tape, so as to prevent a gap from being formed therebetween.

The lining member 80 formed in a thin plate shape thinner than the buffer member 90, which will be described later, that is, in a sheet shape, is disposed on the back side of the upper exterior body 10, that is, between the upper exterior member 10, and the buffer member 90 or the battery holder 95. In order to suppress wrinkles in the upper exterior body 10, one surface of the lining member 80 is stuck on and attached to the back surface of the upper exterior body 10 by, for example, a double-sided tape. The lining member 80 is formed to have a flexibility (bendable) in an operating direction of the power switch 406 (for example, in a pressing direction), by a resin material having flexibility such as PET, for example. Note that, the lining member 80 may be formed of a thin metal plate or the like.

In the lining member 80, a through-hole 80a inside which the power switch 406 is housed in a plan view is formed, in a thickness direction. Note that, a circumference of the through-hole 80a may be completely closed, or need not be completely closed. The through-hole 80a of the lining member 80 is made to be smaller than an outside diameter of a fingertip for an entirety of the fingertip not to enter, and is formed to have a size such that a pad of the fingertip enters so that the power switch 406 can be pushed. More specifically, since an outer diameter of a fingertip differs depending on a person, an inner diameter of the through-hole 80a can be, for example, set in a range of about 10 to 20 mm, and can be set in a range of about 13 to 16 mm. Note that, when a thickness of the upper exterior body 10 is large (for example, about 2 mm or more), the inner diameter of the through-hole 80a can be made to be larger in accordance with the thickness of the upper exterior body 10.

Between the upper surface of the wiring substrate 40 and the lining member 80, the buffer member 90 having buffering properties and formed in a plate shape is disposed. The buffer member 90 is formed to be thicker than a height from a mounting surface of the wiring substrate 40 of the power switch 406 mounted in or on the wiring substrate 40, and a height from a mounting surface of the wiring substrate 40 of an electronic component. The buffer member 90 is stuck on and attached to the other surface of the lining member 80 by, for example, a double-sided tape or the like.

In the buffer member 90, a through-hole 90a inside which the power switch 406 is housed in a plan view is formed in a thickness direction. The through-hole (cavity) 90a formed in the buffer member 90 is formed and disposed, so as to fit inside the through-hole (cavity) 80a formed in the lining member 80 in a plan view. That is, the through-hole 90a of the buffer member 90 is formed to be smaller than the through-hole 80a of the lining member 80. Additionally, each of the through-hole 90a formed in the buffer member 90 and the through-hole 80a formed in the lining member 80 is formed in a substantially circular shape (including a substantially elliptical shape, for example), and each inner diameter is set to be smaller than the outer diameter of the fingertip. More specifically, an inner diameter of the through-hole 90a of the buffer member 90 can be, set in a range of, for example, about 8 to 18 mm, and can be set in a range of about 11 to 14 mm. Note that, when the upper exterior body 10 is thick (for example, a thickness of about 2 mm or more), the inner diameter of the through-hole 90a can be increased in accordance with the thickness.

The sticking member 60 is configured to include the first adhesive layer 601 (corresponding to an adhesive member described in the claims) stuck on an outer surface of the lower exterior body 20, a ventilation layer 603 stuck on the first adhesive layer 601 and having permeability (that is, a moisture permeable layer that passes through moisture), and a second adhesive layer 602 stuck on the ventilation layer 603.

The first adhesive layer 601 has adhesiveness and is light-transmissive, and is stuck on the lower exterior body 20 that is light-transmissive. As the first adhesive layer 601, for example, a double-sided tape can be suitably used. Detection light scattered by a first scattering portion 603a is incident on the first adhesive layer 601. The incident detection light propagates while being reflected in the first adhesive layer 601.

Here, a refractive index of the first adhesive layer 601 is set to be smaller than a refractive index of the skin of the living body, in order to transfer the detection light propagating in the first adhesive layer 601 to a side of the living body (skin). In addition, the refractive index of the first adhesive layer 601 is set to be larger than a refractive index of the lower exterior body 20, in order to collect detection light propagating in the lower exterior body 20 in the first adhesive layer 601. Note that, as resin having a low refractive index, although a fluorine resin or silicone is typical, polypropylene, acrylic and the like may also be included. For example, when silicone is used for the lower exterior body 20, and acrylic is used for an adhesive of the first adhesive layer 601, the refractive indices can be set such that "a refractive index of a horny cell layer of the living body" (for example, about 1.5)>the refractive index of the first adhesive layer 601 (for example, about 1.4 to 1.45)>the refractive index of the lower exterior body 20".

Here, since light has characteristics of passing a portion having a high refractive index, by setting the refractive indices in this manner, the detection light propagating while being reflected in the lower exterior body 20 gradually transfers toward the first adhesive layer 601. Meanwhile, the detection light propagating while being reflected in the first adhesive layer 601 gradually transfers toward the skin, when the first adhesive layer 601 is in contact with the skin of the living body. That is, an amount of light of the detection light propagating in the first adhesive layer 601 decreases. Note that, in the first adhesive layer 601, a through-hole for scattering the detection light may be formed in a thickness direction, in a region opposed to the light receiving unit 46 to be described later.

Incidentally, when the deep body thermometer 1 is used while being stuck on the skin, and sweat remains between the skin and the deep body thermometer 1 (the lower exterior body 20) for a long time, although there is a possibility that the skin is inflamed, by providing the ventilation layer 603 for passing moisture in the sticking member 60, stuffiness due to sweat or the like is suppressed. As the ventilation layer 603, for example, a non-woven fabric can be suitably used. Note that, instead of the non-woven fabric, cloth or knitted fabric may be used. Further, paper, wood, sponge/open-cell foam material, or the like may be used, or a structure made of plastic, rubber, or metal formed with grooves or holes extending from a center of the body temperature measuring unit 15 toward a periphery thereof may be used.

Since the ventilation layer 603 contains air inside thereof, thermal conductivity is usually low. Thus, when the ventilation layer 603 is interposed between the skin and the sensors or the like, body temperature measurement accuracy is affected. Thus, in order to stably measure a body temperature, the ventilation layer 603 is not disposed on respective regions overlapping with the first temperature sensor 701, the third temperature sensor 703 for measuring a temperature of the skin, and the thermal homogenizing patterns connected to the sensors.

Here, a case where the non-woven fabric is used as the ventilation layer 603 will be described as an example. Respective double-sided tapes (the first adhesive layer 601 and second adhesive layer 602) having biocompatibility are stuck on both surfaces of the non-woven fabric (the ventilation layer 603). The ventilation layer 603 and the second adhesive layer 602 are formed with through-holes 60a and 60b in a thickness direction, and, in a plan view, the first temperature sensor 701 and the third temperature sensor 703 fit inside the through-hole 60a and the through-hole 60b, respectively.

In addition, usually, since the double-sided tape (second adhesive layer 602) is inferior in moisture permeability to the non-woven fabric (ventilation layer 603), a plurality of through-holes 60c formed in the thickness direction can be formed at least in the second adhesive layer 602. In this case, for example, the through-holes 60c having a diameter of about 1 to 10 mm, can be arranged at intervals of about 2 to 20 mm.

When the non-woven fabric is used as the ventilation layer 603, the ventilation layer 603 functions as a scattering portion that scatters the detection light. This is because, when the first adhesive layer 601 and the ventilation layer 603 are in close contact with each other, scattering occurs at an interface. The ventilation layer 603 integrally includes the first scattering portion 603a disposed in a region opposed to the light emitting unit 45, and the second scattering portion 603b disposed in a region opposed to the light receiving unit 46. The first scattering portion 603a scatters the detection light emitted from the light emitting unit 45. Part of the detection light scattered by the first scattering portion 603a enters the first adhesive layer 601. The second scattering portion 603b scatters the detection light propagated in the first adhesive layer 601. Part of the detection light scattered by the second scattering portion 603b is transmitted through the lower exterior body 20 and enters the light receiving unit 46.

As described above, the ventilation layer 603 and the second adhesive layer 602 are formed with the through-holes 60a and 60b in the thickness direction, and, in a plan view, the first temperature sensor 701 and the third temperature sensor 703 fit inside the through-hole 60a and the through-hole 60b, respectively. Thus, in a plan view, there is a region in which the first scattering portion 603a and the second scattering portion 603b are not provided, between the light emitting unit 45 and the light receiving unit 46. Note that, instead of the non-woven fabric, for example, a resin film or a resin tape that has fine particles for light diffusion or in which fine patterns for light diffusion are printed on a surface thereof, an adhesive with fine particles for light diffusion, paper sheet or the like may also be used as the scattering portion. The fine particles/fine patterns for light diffusion may also be formed inside the first adhesive layer 601, in a vicinity of the light emitting unit 45 and the light receiving unit 46.

Note that, instead of each of the first scattering portion 603a made of the non-woven fabric disposed in the region opposed to the light emitting unit 45, and the second scattering portion 603b made of the non-woven fabric disposed in the region opposed to the light receiving unit 46, a through-hole or a slit may be formed in the thickness direction of the first adhesive layer 601 to function as a scattering portion. Additionally, instead of each of the first scattering portion 603a made of the non-woven fabric disposed in the region opposed to the light emitting unit 45 and the second scattering portion 603b made of the non-woven fabric disposed in the region opposed to the light receiving unit 46, an end face of the first adhesive layer 601 may be disposed to function as a scattering portion.

As described above, the arithmetic processor 43 is constituted by, for example, a micro control unit (MCU), an EEPROM, a RAM, and the like, calculates a deep body temperature based on detection values (temperature data) of each temperature sensor 70 read, through the sensor input unit 42, and detects a contact state of the deep body thermometer 1 with the living body and attachment/detachment. Additionally, the arithmetic processor 43 stores calculated deep body temperature data, contact state information, and the like in a memory such as a RAM. Further, the arithmetic processor 43 outputs the calculated deep body temperature data, the contact state information, and the like to the wireless communication unit 403, to wirelessly transmit to the external management device/management system 3.

In particular, the arithmetic processor 43 has a function of reliably determining whether or not the deep body thermometer 1 is in contact with the living body, in particular, even in a state of being slightly separated from the living body surface. Thus, the arithmetic processor 43 includes a deep body temperature calculation unit 431, a contact state determination unit 432, and a power controller 433 in terms of function. In the arithmetic processor 43, a program stored in an EEPROM or the like is executed by an MCU to realize functions of the deep body temperature calculation unit 431, the contact state determination unit 432, and the power controller 433.

The deep body temperature calculation unit 431 calculates (estimates) a deep body temperature, based on a temperature difference between front and back sides of each of the thermal resistors 301 and 302, caused by a difference between two heat fluxes formed by using the two thermal resistors 301 and 302 having different thermal resistance. More specifically, the deep body temperature calculation unit 431 calculates a deep body temperature Tb, based on, for example, the following equation (1).

$$Tb=\{T1(T3-T4)*Ra1-T3(T1-T2)*Ra2\}/\{(T3-T4)*Ra1-(T1-T2)*Ra2\} \quad (1)$$

Note that, Tb indicates the deep body temperature, T1 indicates a first temperature detected by the first temperature sensor 701, T2 indicates a second temperature detected by the second temperature sensor 702, and Ra1 indicates a thermal resistance value of the first thermal resistor 301. In addition, T3 indicates a third temperature detected by the third temperature sensor 703, T4 indicates a fourth temperature detected by the fourth temperature sensor 704, and Ra2 indicates a thermal resistance value of the second thermal resistor 302.

Here, since Ra1 and Ra2 are known, the deep body temperature Tb can be uniquely determined by detecting the four temperatures (T1, T2, T3, and T4).

The contact state determination unit 432 determines a contact state between the stick-on deep body thermometer 1 and the living body surface, based on a light receiving amount of detection light received by the light receiving unit 46 and/or a change in the light receiving amount. More specifically, when the light receiving amount of the detection light received by the light receiving unit 46 is less than a predetermined value, the contact state determination unit 432 determines that the stick-on deep body thermometer 1 and the living body surface are in contact with each other at least on an optical path of the detection light, that is, that the contact state is normal. On the other hand, when the light receiving amount of the detection light received by the light receiving unit 46 is equal to or more than the predetermined value, the contact state determination unit 432 determines that the stick-on deep body thermometer 1 and the living body surface are not in contact with each other at least on the optical path of the detection light, that is, that all or part of the stick-on deep body thermometer 1 is not in contact with the living body surface, and that the contact state is abnormal.

In addition, when the light receiving amount of the detection light received by the light receiving unit 46 decreases by a predetermined value or more, the contact state determination unit 432 determines that the stick-on deep body thermometer 1 is normally stuck on the living body surface. On the other hand, when the light receiving amount of the detection light received by the light receiving unit 46 increases by a predetermined value or more, the contact state determination unit 432 determines that all or part of the stick-on deep body thermometer 1, that is, at least a portion on the optical path of the detection light, is separated off from the living body surface.

Note that, the body temperature data (deep body temperature Tb) acquired by the deep body temperature calculation unit 431, the contact state information determined by the contact state determination unit 432, and the like are outputted to the wireless communication unit 403 and the like. As described above, when contact/non-contact of the deep body thermometer 1 is detected, the wireless communication unit 403 transmits the contact state information indicating the contact state of the deep body thermometer 1 with the living body to the external management device/management system 3. When the contact/non-contact of the deep body thermometer 1 is detected, the wireless communication unit 403 notifies the portable terminal 5 for the supervisor of the contact state information via the management device/management system 3.

When determining that the deep body thermometer 1 is detached from the living body and when determining as non-contact, the power controller 433 (corresponding to a power controller described in the claims) determines that measurement is impossible, and shifts the deep body thermometer 1 to a low power consumption mode (sleep mode), or turns power supply of the deep body thermometer 1 off.

Figure 5:
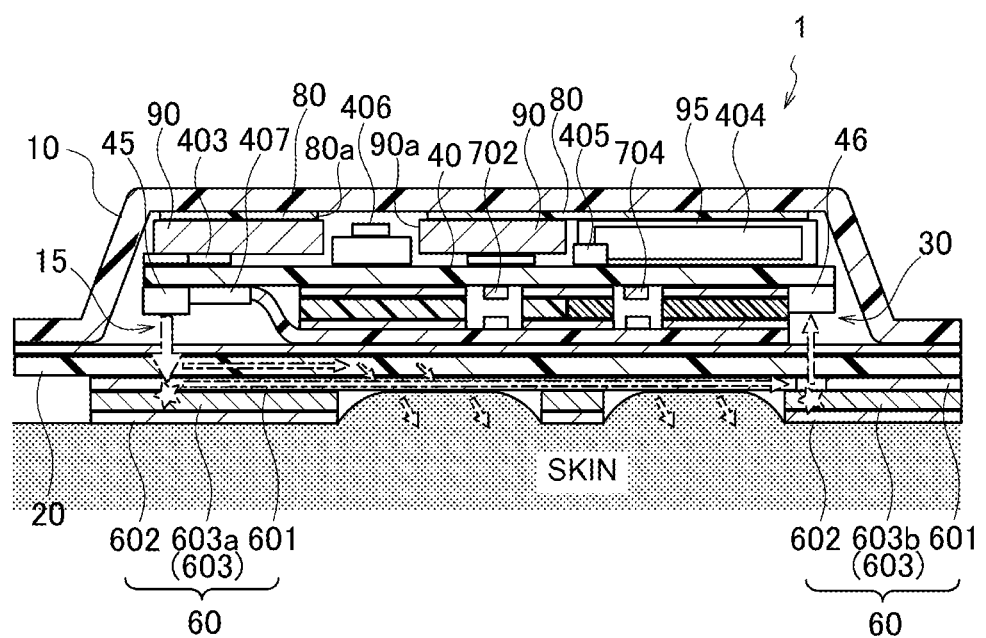
FIG. 5 is a diagram for explaining operation of the stick-on deep body thermometer according to the first embodiment.

Next, operation of the stick-on deep body thermometer 1 will be described with reference to FIG. 5. FIG. 5 is a diagram for explaining the operation of the stick-on deep body thermometer 1. With the configuration as described above, in the stick-on deep body thermometer 1, pulsing detection light is first emitted from the light emitting unit 45 toward a direction of the lower exterior body 20. The detection light emitted from the light emitting unit 45, after being transmitted through the lower exterior body 20, is scattered by the first scattering portion 603a, and part thereof enters the first adhesive layer 601. The detection light entering the first adhesive layer 601, after propagated from a side of the light emitting unit 45 to a side of the light receiving unit 46 in the first adhesive layer 601, is scattered by the second scattering portion 603b. Part of the detection light scattered by the second scattering portion 603b is transmitted through the lower exterior body 20 and reaches the light receiving unit 46, and is received by the light receiving unit 46.

Incidentally, since the refractive index of the skin is closer to the refractive index of the first adhesive layer 601 compared to the air, when the body surface of the living body comes in contact with the first adhesive layer 601 as illustrated in FIG. 5, leakage of the detection light to a side of the living body increases, and an amount of light received by the light receiving unit 46 decreases. In particular, as described above, since the refractive indices are set to satisfy "refractive index of the horny cell layer of the living body>refractive index of the first adhesive layer 601>refractive index of the lower exterior body 20", the detection light propagating while being reflected in the lower exterior body 20 gradually transfers toward the first adhesive layer 601. On the other hand, the detection light propagating while being reflected in the first adhesive layer 601 gradually transfers toward the living body, when the first adhesive layer 601 is in contact with the body surface of the living body. That is, an amount of light of the detection light propagating in the first adhesive layer 601 decreases. As a result, when the light receiving amount of the detection light received by the light receiving unit 46 is less than the predetermined value, it is determined that the stick-on deep body thermometer 1 and the living body surface are in contact with each other at least on the optical path of the detection light, that is, that the contact state is normal. On the other hand, when the light receiving amount of the detection light received by the light receiving unit 46 is equal to or more than the predetermined value, it is determined that the stick-on deep body thermometer 1 and the living body surface are not in contact with each other at least on the optical path of the detection light, that is, that the contact state is abnormal. Further, when the light receiving amount of the detection light received by the light receiving unit 46 decreases by the predetermined value or more, it is determined that the stick-on deep body thermometer 1 and the living body surface normally come in contact with each other at least on the optical path of the detection light, and when the light receiving amount of the detection light received by the light receiving unit 46 increases by the predetermined value or more, it is determined that all or part of the stick-on deep body thermometer 1, that is, at least a portion on the optical path of the detection light, is separated from the living body surface.

As described in detail above, according to the present embodiment, the detection light emitted from the light emitting unit 45 is scattered by the first scattering portion 603a, and enters the first adhesive layer 601. Then, after propagating in the first adhesive layer 601, the detection light is scattered by the second scattering portion 603b, transmitted through the lower exterior body 20, reaches the light receiving unit 46, and is received by the light receiving unit 46. Incidentally, since the refractive index of the skin is closer to the refractive index of the first adhesive layer 601 compared to air, when the body surface comes in contact with the first adhesive layer 601, leakage of the detection light to the body surface increases, and the amount of light received by the light receiving unit 46 decreases. Thus, when the light receiving amount of the received detection light is less than the predetermined value, it is possible to determine that the first adhesive layer 601, that is, the stick-on deep body thermometer 1, and the living body surface are normally in contact with each other, and when the light receiving amount of the received detection light is equal to or more than the predetermined value, it is possible to determine that the contact state between the stick-on deep body thermometer 1 and the living body surface is abnormal. As a result, it is possible to reliably determine whether or not the stick-on deep body thermometer 1 is in contact with the living body, in particular, even in a state of being slightly separated from the living body surface.

Further, according to the present embodiment, when the light receiving amount of the detection light received by the light receiving unit 46 decreases by a predetermined value or more, it is determined that the stick-on deep body thermometer 1 and the living body surface normally come in contact with each other, and when the light receiving amount of the detection light received by the light receiving unit 46 increases by a predetermined value or more, it is determined that all or part of the stick-on deep body thermometer 1 is separated from the living body surface. Thus, it is possible to reliably detect attachment and detachment of the deep body thermometer 1, that is, sticking and separation.

According to the present embodiment, each of the first scattering portion 603a disposed in the region opposed to the light emitting unit 45, and the second scattering portion 603b disposed in the region opposed to the light receiving unit 46 is made of the non-woven fabric stuck on the first adhesive layer 601. In this way, by using the non-woven fabric, it is possible to efficiently scatter the detection light.

According to the present embodiment, the refractive index of the first adhesive layer 601 is set to be smaller than the refractive index (for example, about 1.5) of the horny cell layer of the skin of the living body. Since the light is more likely to propagate in a portion having a higher refractive index, light leakage increases when the skin comes in contact with the deep body thermometer 1, so that the contact detection performance is improved.

According to the present embodiment, the refractive index of the first adhesive layer 601 is set to be larger than the refractive index of the lower exterior body 20. As described above, since light is more likely to propagate in the portion having a higher refractive index, light propagation in the lower exterior body 20 is suppressed, and light leakage sensitivity increases when the skin comes in contact with the deep body thermometer 1, so that the contact detection performance is improved.

According to the present embodiment, the first adhesive layer 601 is a double-sided tape. Here, although a layer that comes in contact with the living body (skin) needs to be a light-transmissive layer, by using a double-sided tape having adhesiveness for the layer in contact, the layer can be in close contact with the skin well, and the contact is stabilized.

According to the present embodiment, in a plan view, there is a region in which the first scattering portion 603a and the second scattering portion 603b are not provided, between the light emitting unit 45 and the light receiving unit 46. Here, when a scattering portion exists between and across the light emitting unit 45 and the light receiving unit 46, although part of light propagates due to scattering and light leakage reduces even when the skin comes in contact with the deep body thermometer 1, thus there is a possibility that the detection accuracy decreases, such a decrease in the detection accuracy can be suppressed, by providing a region in which no scattering portion is present.

According to the present embodiment, the lower exterior body 20 is translucent. Here, since the lower exterior body 20 is not directly contact with the living body, an amount of detection light leaking out from the lower exterior body 20 to the living body is relatively small. Thus, by making the lower exterior body 20 translucent, and suppressing propagation of the detection light in the lower exterior body 20, sensitivity can be improved.

According to the present embodiment, the light emitting unit 45 emits detection light that is visible light. Incidentally, since the visible light is light having a wave length that is largely absorbed by the skin, the detection light entering the skin is almost prevented from returning to the first adhesive layer 601, so that leakage of the detection light increases, and the contact detection performance improves. In particular, since the skin has very high absorbance for green and blue, when a wave length of the detection light is set to a wave length of green or blue, the detection light is more likely to be absorbed by the skin, and the contact detection performance can be improved.

According to the present embodiment, the light emitting unit 45 emits pulsing detection light. As described above, since pulse emission is performed, the power consumption of the light emitting unit 45 can be reduced, and the life of the battery 404 can be extended.

According to the present embodiment, the contact state information indicating the contact state of the deep body thermometer 1 with the living body is transmitted to the management device/management system 3. Thus, when the deep body thermometer 1 is detached from the body surface, the detachment can be notified.

According to the present embodiment, the contact state information of the deep body thermometer 1 is notified to the portable terminal 5 for the supervisor via the management device/management system 3. Thus, when the deep body thermometer 1 is detached from the body surface, the detachment can be notified to the supervisor.

According to the present embodiment, when the deep body thermometer 1 is determined to be detached from the living body, the deep body thermometer 1 is shifted to the low power consumption mode, or turns the power supply off. Thus, when the deep body thermometer 1 is detached, it is possible to partially stop functions, or turn the power supply off to reduce power consumption.

Modified Example

Figure 6:
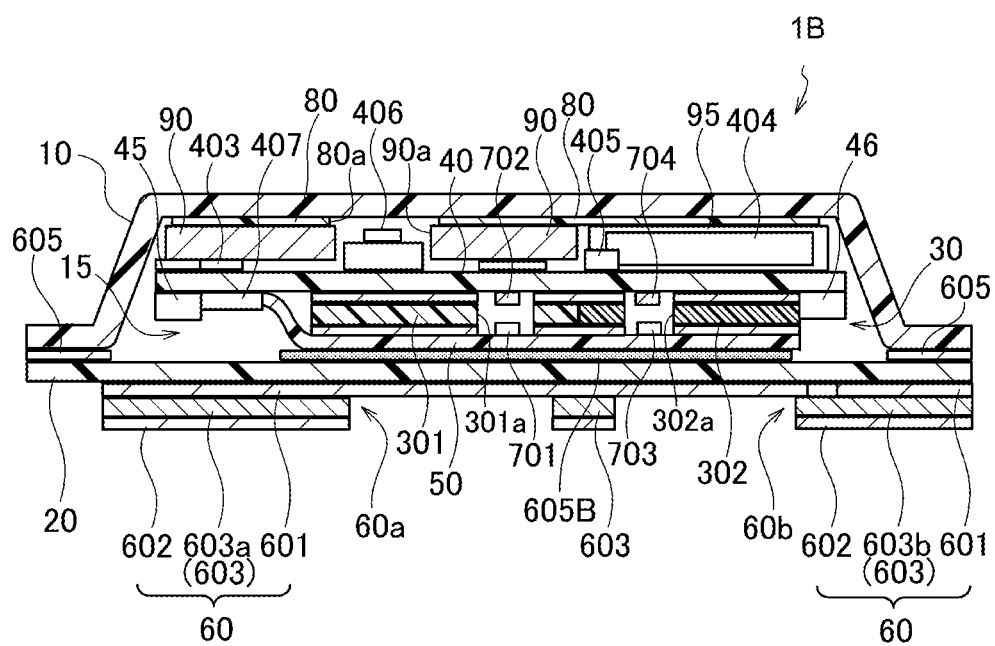
FIG. 6 is a sectional view illustrating a configuration of a stick-on deep body thermometer according to a modification example.
Figure 7:
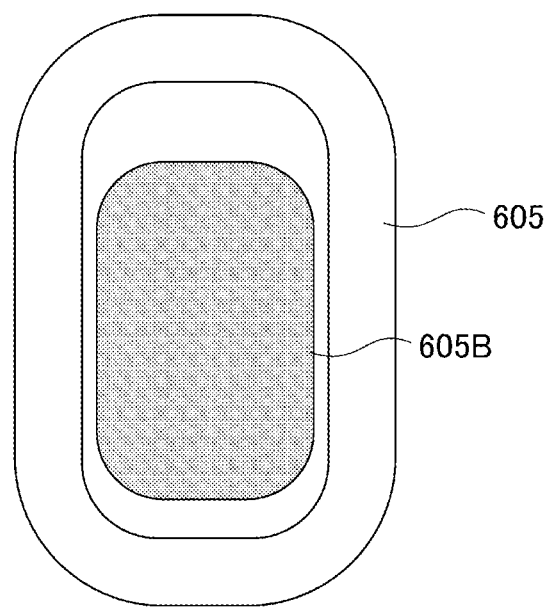
FIG. 7 is a plan view illustrating a double-sided tape constituting the stick-on deep body thermometer according to the modification example.
Figure 8:
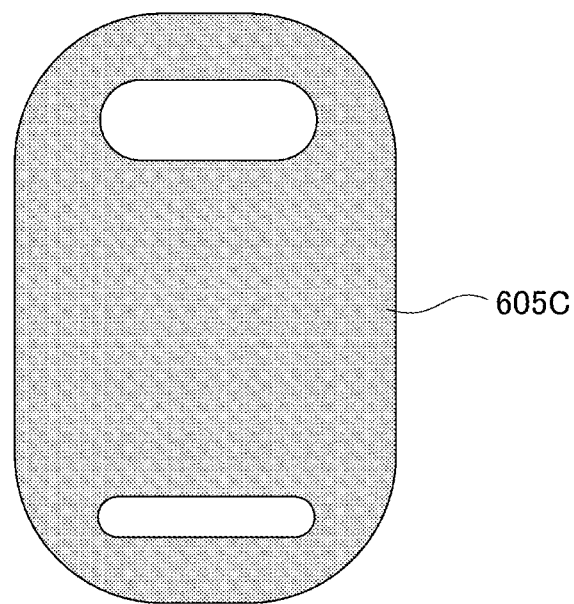
FIG. 8 is a plan view illustrating another double-sided tape constituting the stick-on deep body thermometer according to the modification example.

Next, with reference to FIGS. 6 to 8 in combination, a description will be given of a stick-on deep body thermometer 1B according to a modification example. FIG. 6 is a sectional view illustrating a configuration of the stick-on deep body thermometer 1B. FIG. 7 is a plan view illustrating a double-sided tape 605B constituting the stick-on deep body thermometer 1B. FIG. 8 is a plan view illustrating another double-sided tape 605C constituting the stick-on deep body thermometer 1B.

The stick-on deep body thermometer 1B is different from the stick-on deep body thermometer 1 according to the first embodiment described above, in that the double-sided tape 605B used for adhesion of the lower exterior body 20 is, for example, made of a material having a high light absorption property such as a black material. That is, in the stick-on deep body thermometer 1B, the double-sided tape 605B (corresponding to a light-absorbing member described in the claims) having a high light absorption property is stuck on the lower exterior body 20, between the light emitting unit 45 and the light receiving unit 46 in a plan view. A material having a high light absorption property is used for the double-sided tape 605B in contact with the lower exterior body 20 to reduce detection light propagating in the lower exterior body 20, thereby improving contact detection performance.

More specifically, as illustrated in FIG. 7, the double-sided tape 605B having the high light absorption property is used between the light emitting unit 45 and the light receiving unit 46, as a double-sided tape for sticking the upper exterior body 10 and the lower exterior body 20. Note that, for a peripheral edge portion, a waterproof double-sided tape that is light-transmissive may be used. Alternatively, as illustrated in FIG. 8, the double-sided tape 605C having a light absorption property and formed with openings in regions opposed to each of the light emitting unit 45 and the light receiving unit 46 may be used, as a double-sided tape for sticking the upper exterior body 10 and the lower exterior body 20. Note that, since other configurations are the same as or similar to those of the stick-on deep body thermometer 1 according to the first embodiment described above, detailed description thereof will be omitted.

Incidentally, when light is propagated while being reflected, and a member having a high light absorption property is provided on a reflection surface, the light is absorbed by the member. Thus, according to the present modification, the detection light propagating while reflected inside the lower exterior body 20 is absorbed by the double-sided tape 605B stuck on the lower exterior body 20 and having the light absorption property, so that the contact detection performance is improved.

Second Embodiment

Figure 9:
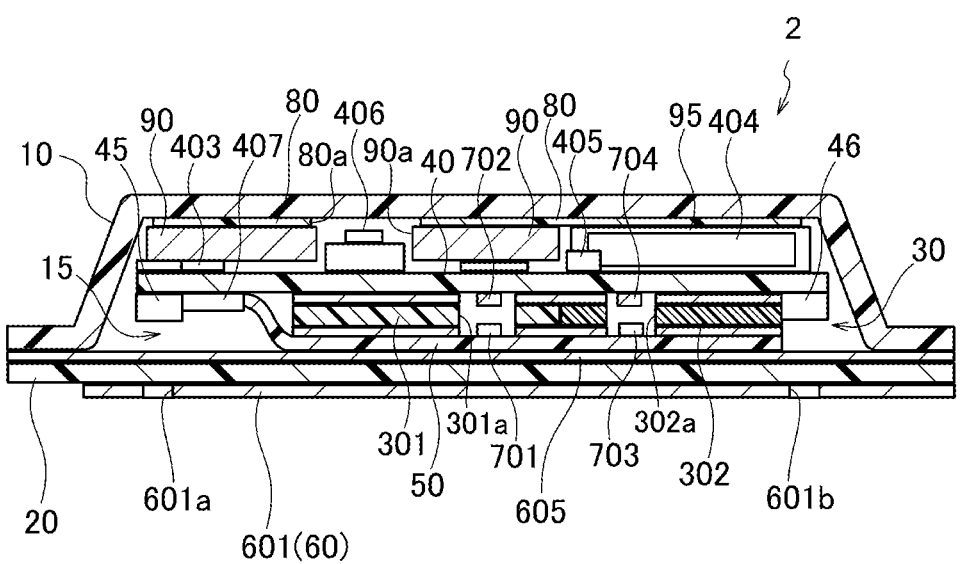
FIG. 9 is a sectional view illustrating a configuration of a stick-on deep body thermometer according to a second embodiment.

Next, a stick-on deep body thermometer 2 according to a second embodiment will be described with reference to FIG. 9. FIG. 9 is a sectional view illustrating a configuration of the stick-on deep body thermometer 2. The stick-on deep body thermometer 2 is different from the stick-on deep body thermometer 1 according to the first embodiment described above, in that the second adhesive layer 602 and the ventilation layer (non-woven fabric) 603, that is, the first scattering portion 603a and the second scattering portion 603b are not included. Additionally, the stick-on deep body thermometer 2 is different from the stick-on deep body thermometer 1 according to the first embodiment described above, in that a first through-hole 601a for scattering detection light is formed in a thickness direction, in a region of the first adhesive layer 601, opposed to the light emitting unit 45. Similarly, the stick-on deep body thermometer 2 is different from the stick-on deep body thermometer 1 according to the first embodiment described above, in that a second through-hole 601b for scattering the detection light is formed in a thickness direction, in a region of the first adhesive layer 601, opposed to the light receiving unit 46.

Here, since a side surface of each of the first through-hole 601a and the second through-hole 601b has irregularities when viewed microscopically, these through-holes effectively function as scattering portions for scattering the detection light. Note that, a configuration may be adopted in which, instead of the first through-hole 601a and the second through-hole 601b, a slit is provided, or an end face of the first adhesive layer 601 is disposed. In this case, the slit or the end face serves as a scattering portion. Since other configurations are the same as or similar to those of the stick-on deep body thermometer 1 according to the first embodiment described above, detailed description thereof will be omitted.

According to the present embodiment, since the first through-hole 601a and the second through-hole 601b function as the scattering portions, it is possible to reliably determine whether the stick-on deep body thermometer 2 is in contact with the living body or not, similarly to the stick-on deep body thermometer 1 according to the first embodiment described above, without necessarily including the ventilation layer 603 described above, that is, the first scattering portion 603a and the second scattering portion 603b, particularly even in a state of being slightly separated from the living body surface.

While the embodiments of the present disclosure have been described above, the present disclosure is not limited to the embodiments described above, and various modifications may be made. For example, in the above embodiments, the case is described as the example in which although the present disclosure is applied to the two heat flux type deep body thermometer, the present disclosure may be applied to a one heat flux type deep body thermometer. Further, application to a body thermometer other than a deep body thermometer is also possible. Furthermore, the present disclosure can also be applied to, for example, an electrocardiograph, and a stick-on device for living body having a vital sensor for measuring respiration and pulse.

In addition, a configuration may be adopted in which an amount of light of disturbance light is detected from a light receiving amount when the light emitting unit 45 does not emit detection light, and a contact state with the living body is determined in consideration of the amount of light of the disturbance light.

Further, a configuration may also be adopted in which one more light receiving unit 46 is added, to determine a contact state with the living body by using one light emitting unit 45 and two light receiving units 46. Alternatively, a configuration may be adopted in which two sets of the light emitting unit 45 and the light receiving unit 46 are used. In this way, it is possible to determine a contact state with the living body in more detail.

Further, instead of the configuration in which detection light is scattered, incident on the first adhesive layer 601, and emitted from the first adhesive layer 601, for example, a configuration may be adopted in which an angle of light is changed by using a mirror or the like. Further, for example, gel or the like may be used for the first adhesive layer 601, instead of the double-sided tape.

While embodiments of the disclosure have been described above, it is to be understood that variations and modifications will be apparent to those skilled in the art without necessarily departing from the scope and spirit of the disclosure. The scope of the disclosure, therefore, is to be determined solely by the following claims.

What is claimed is:

1. A stick-on device having an upper exterior body and a light-transmissive lower exterior body, and being configured to stick to a living body, the stick-on device comprising:
    a light emitter disposed inside the stick-on device between the upper exterior body and the lower exterior body, and being configured to emit a detection light;
    a first scattering layer configured to scatter the detection light transmitted through the lower exterior body;
    an adhesive layer that is light-transmissive and attached to the lower exterior body, the detection light scattered by the first scattering layer being incident to the adhesive layer;
    a second scattering layer configured to scatter detection light propagated in the adhesive layer;
    a light receiver disposed inside the stick-on device between the upper exterior body and the lower exterior body, and being configured to receive detection light that is scattered by the second scattering layer, transmitted through the lower exterior body, and incident on the light receiver; and
    a processor configured to:
        when an amount of detection light received by the light receiver is less than a predetermined value, determine that a contact state between the stick-on device and the living body is normal, and
        when the amount of detection light received by the light receiver is equal to or greater than the predetermined value, determine that the contact state between the stick-on device and the living body is abnormal.

2. The stick-on device according to claim 1, wherein the processor is further configured to:
    when the amount of detection light received by the light receiver decreases by at least a second predetermined value, determine that the stick-on device and the living body normally come in contact with each other, and
    when the amount of detection light received by the light receiver increases by at least a third predetermined value, determine that all or part of the stick-on device is separated from a living body surface.

3. The stick-on device according to claim 1, wherein the adhesive layer comprises a hole at a location opposed to the light receiver.

4. The stick-on device according to claim 1, wherein:
    the first scattering layer is disposed at a location opposed to the light emitter,
    the second scattering layer is disposed at a location opposed to the light receiver, and
    the first scattering layer and the second scattering layer are each non-woven fabric layers attached to the adhesive layer.

5. The stick-on device according to claim 1, wherein:
    the first scattering layer is disposed at a location opposed to the light emitter,
    the second scattering layer is disposed at a location opposed to the light receiver, and
    the first scattering layer and the second scattering layer are each holes formed through the adhesive layer.

6. The stick-on device according to claim 1, wherein:
    the first scattering layer is disposed at a location opposed to the light emitter,
    the second scattering layer is disposed at a location opposed to the light receiver, and
    the first scattering layer and the second scattering layer are a side surface of an outer edge of the adhesive layer.

7. The stick-on device according to claim 1, wherein a refractive index of the adhesive layer is less than 1.5.

8. The stick-on device according to claim 1, wherein a refractive index of the adhesive layer is greater than a refractive index of the lower exterior body.

9. The stick-on device according to claim 1, wherein the adhesive layer is a double-sided tape.

10. The stick-on device according to claim 1, wherein, as seen in a plan view, the first scattering layer and the second scattering layer do not overlap a portion of the lower exterior body between the light emitter and the light receiver.

11. The stick-on device according to claim 1, wherein the lower exterior body is translucent.

12. The stick-on device according to claim 1, further comprising a light-absorbing layer in contact with the lower exterior body, wherein, as seen in a plan view, the light-absorbing layer is located between the light emitter and the light receiver.

13. The stick-on device according to claim 1, wherein the detection light is visible light.

14. The stick-on device according to claim 1, wherein the light emitter is configured to emit the detection light as a pulsed detection light.

15. The stick-on device according to claim 1, wherein the light emitter and the light receiver are mounted in or on a wiring substrate so as to face the lower exterior body.

16. The stick-on device according to claim 1, further comprising:
    a vital sign sensor.

17. The stick-on device according to claim 1, wherein the stick-on device is a stick-on thermometer having a temperature sensor.

18. The stick-on device according to claim 1, further comprising:
    a transmitter configured to transmit, to an external device, contact state information indicating the determined contact state of the stick-on device with the living body.

19. The stick-on device according to claim 18, wherein the transmitter is configured to notify a portable terminal about the contact state of the stick-on device via the external device.

20. The stick-on device according to claim 1, further comprising:
    a power controller configured to shift the stick-on device to a low power consumption mode or to turn off a power supply when the processor determines the stick-on device is not in contact with the living body.

* * * * *